(12) United States Patent
Vandse

(10) Patent No.: US 7,955,622 B2
(45) Date of Patent: Jun. 7, 2011

(54) CONTROLLED-RELEASE GALANTAMINE FORMULATIONS

(75) Inventor: Sunil Vandse, Piscataway, NJ (US)

(73) Assignee: Actavis Group PTC HF (IS)

( * ) Notice: Subject to any disclaimer, the term of this patent is extended or adjusted under 35 U.S.C. 154(b) by 500 days.

(21) Appl. No.: 11/870,444

(22) Filed: Oct. 11, 2007

(65) Prior Publication Data
US 2008/0254131 A1   Oct. 16, 2008

Related U.S. Application Data

(60) Provisional application No. 60/829,311, filed on Oct. 13, 2006.

(51) Int. Cl.
A61K 9/16 (2006.01)
A61K 9/00 (2006.01)
A61P 25/34 (2006.01)

(52) U.S. Cl. ......... 424/468; 424/400; 424/490; 514/215

(58) Field of Classification Search .................. None
See application file for complete search history.

(56) References Cited

U.S. PATENT DOCUMENTS

2005/0191349 A1* 9/2005 Boehm et al. ................. 424/464
2007/0092568 A1  4/2007 Gore et al.
2009/0087488 A1* 4/2009 Verma et al. .................. 424/472

FOREIGN PATENT DOCUMENTS

| WO | 00/38686 | * | 12/1999 |
| WO | 00/38686 | * | 7/2000 |
| WO | 0038686 | A1 | 7/2000 |
| WO | 2005065661 | A2 | 7/2005 |
| WO | 20070029081 | A1 | 3/2007 |

OTHER PUBLICATIONS

Particle Size Conversion Table.*
Particle Size Conversion table.*
International Searching Authority, International Search Report PCT/US2007/021736, Filing date: Oct. 11, 2007, Mailing date: Apr. 22, 2008, 7 pages.
International Searching Authority, Written Opinion PCT/US2007/021736, Filing date: Oct. 11, 2007, Mailing date: Apr. 22, 2008, 9 pages.

* cited by examiner

*Primary Examiner* — Robert A Wax
*Assistant Examiner* — Suzanne Ziska
(74) *Attorney, Agent, or Firm* — Cantor Colburn LLP

(57) ABSTRACT

Controlled-release galantamine formulations, including controlled-release particles, pellets, granules, and spheres are described. Controlled-release particles, pellets, granules, and spheres with immediate release top-coat are also described. Method of preparing such formulations and method of treating a variety of disorders are also disclosed.

19 Claims, No Drawings

CONTROLLED-RELEASE GALANTAMINE FORMULATIONS

CROSS-REFERENCE TO RELATED APPLICATIONS

This application claims the benefit of U.S. Provisional Application Ser. No. 60/829,311 filed Oct. 13, 2006, which is incorporated herein by reference in its entirety.

BACKGROUND

Galantamine (I) ((4aS,6R,8aS)-4a,5,9,10,11,12-hexahydro-3-methoxy-11-methyl6H-benzofuro[3a,3,2-ef][2]benzazepin-6-ol) is a known reversible,

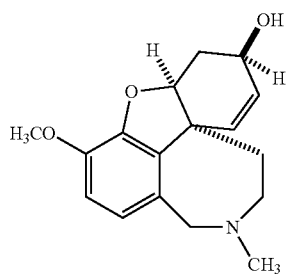

(I)

competitive acetylcholinesterase inhibitor. The compound can be isolated from the bulbs of the Caucasian snowdrops Galantanus woronowi in addition to the common snowdrop Galanthus Nivalis.

Galantamine and its salts have been employed as a pharmaceutically active agent in the treatment of a variety of disorders, including mania, alcoholism, nicotine dependence, and Alzheimer's disease. In particular, galantamine hydrobromide has been used for the treatment of Alzheimer's disease and is currently formulated as film-coated tablets of 4 milligram (mg), 8 mg, and 12 mg base equivalent doses for twice a day oral administration under the trade name RAZADYNE, as well as hard gelatin extended-release capsules of 8 mg, 16 mg, and 24 mg base equivalent doses for once daily oral administration under the trade name RAZADYNE ER.

As an acetylcholinesterase inhibitor, galantamine is known to be active at nicotinic receptor sites, but not on muscarinic receptor sites. It is capable of passing the blood-brain barrier in humans, and presents no severe side effects in therapeutically effective dosages. Although no severe side effects are found, when first dosed, patients may experience the occurrence of numerous side effects, which affect the patients' tolerability of the drug. Side effects, such as nausea or vomiting and headaches, often occur when the drug is introduced at high doses. An initial therapeutic regimen often starts with first introducing galantamine at low doses for several weeks followed by the gradual increase to the optimal active dose for the patient. When the regular dosing of galantamine is interrupted for two or more days, it is recommended to commence dosing at the lowest levels as continuation at the doses prior to the interruption are generally not well tolerated by the patient. Such side effects may result in lack of patient compliance.

Furthermore, certain patient populations, such as Alzheimer's patients, may find it difficult to adhere to a dosing regimen that requires administration of a formulation several times a day. Accordingly, controlled-release formulations of galantamine are a particularly attractive alternative to immediate-release formulations as they can be administered less frequently and can provide more stable blood levels.

Certain controlled-release galantamine compositions are known (see, for example, WO 00/38686). Such compositions include particles containing galantamine and a water soluble excipient, wherein the particles are coated with a release rate controlling membrane coating. However, further improvements in the area of controlled-release formulations may provide improved pharmacokinetic and/or dissolution profiles not yet achieved by known formulations.

There remains a continued need in the art for improved controlled-release galantamine formulations that can be administered once daily or even less frequently.

SUMMARY OF THE INVENTION

In one embodiment, a controlled-release dosage formulation comprises a core comprising galantamine as the active ingredient and a water insoluble polymer, wherein the core is free of a water soluble excipient; and a release rate controlling coating substantially surrounding the core, wherein the release rate controlling coating comprises a release retarding excipient.

In another embodiment, a controlled-release dosage formulation comprises a core comprising galantamine as the active ingredient and a water insoluble polymer, wherein the core is free of a water soluble excipient; a release rate controlling coating substantially surrounding the core, wherein the release rate controlling coating comprises a release retarding excipient; and an immediate release top-coat comprising galantamine and a polymer.

In yet another embodiment, a controlled-release formulation comprises a core comprising a water insoluble polymer and galantamine as the active ingredient, wherein the core is free of a water soluble excipient; and a release rate controlling coating substantially surrounding the core, wherein the release rate controlling coating comprises a release retarding excipient; wherein the formulation exhibits a dissolution profile such that at 1 hour about 4 to about 9% of the galantamine is released, at 2 hours about 15 to about 25% of the galantamine is released, at 4 hours about 40 to about 55% of the galantamine is released, and at 8 hours about 80 to about 100% of the galantamine is released after combining the dosage formulation with 900 ml of pH 6.5 phosphate buffer at 37° C. in USP Type 1 Apparatus (USP, <711> Dissolution), at a paddle speed of 100 rpm.

Also disclosed are methods of preparing controlled-release formulations.

Further disclosed is a method of treating a disorder selected from dementia, mania, or nicotine dependence in a patient in need thereof comprising administering to the patient the dosage above disclosed formulations.

These and other advantages of the dosage formulations disclosed herein, as well as additional inventive features, will be apparent from the description of the invention provided herein.

DETAILED DESCRIPTION OF THE INVENTION

Disclosed herein is a controlled-release dosage formulation comprising a core comprising galantamine as the active ingredient and a water insoluble polymer, wherein the core is free of a water soluble excipient; and a release rate controlling coating substantially surrounding the core, wherein the release rate controlling coating comprises a release retarding excipient.

Also disclosed herein is a controlled-release dosage formulation comprising a core comprising galantamine as the active ingredient and a water insoluble polymer, wherein the core is free of a water soluble excipient; a release rate controlling coating substantially surrounding the core, wherein the release rate controlling coating comprises a release retarding excipient; and an immediate release top-coat comprising galantamine and a polymer.

As used herein, "controlled-release" means a dosage form in which the release of the active agent is controlled or modified over a period of time. Controlled can mean, for example, sustained, delayed or pulsed-release at a particular time. For example, controlled-release can mean that the release of the active ingredient is extended for longer than it would be in an immediate-release dosage form, i.e., at least over several hours.

As used herein, "immediate-release" means a dosage form in which greater then or equal to about 75% of the active ingredient is released within two hours, or, more specifically, within one hour, of administration. Immediate-release or controlled-release may also be characterized by their dissolution profiles.

As used herein, "dissolution profile" means a plot of the cumulative amount of active ingredient released as a function of time. The dissolution profile can be measured utilizing the Drug Release Test <724>, which incorporates standard test USP 26 (Test <711> Dissolution). A profile is characterized by the test conditions selected. Thus the dissolution profile can be generated at a pre-selected apparatus type, shaft speed, temperature, volume, and pH of the dissolution media.

Release forms may also be characterized by their pharmacokinetic parameters. As used herein, "pharmacokinetic parameters" describe the in vivo characteristics of the active ingredient galantamine over time, including for example plasma concentration of the active ingredient. As used herein, "$C_{max}$" means the measured concentration of the active ingredient in the plasma at the point of maximum concentration. "$C_{24}$" means the concentration of the active ingredient in the plasma at about 24 hours. "$T_{max}$" refers to the time at which the concentration of the active ingredient in the plasma is the highest. "AUC" is the area under the curve of a graph of the concentration of the active ingredient (typically plasma concentration) vs. time, measured from one time to another.

As used hereinafter, the active ingredient "galantamine" may be in the form of a free base, or its pharmaceutically acceptable salts, solvates (including hydrates), polymorphs, all optical isomers, or combinations comprising at least one of the foregoing forms of galantamine. In addition, the various forms of galantamine can be in crystalline or non-crystalline (amorphous) forms.

As used herein, "pharmaceutically acceptable salts" of galantamine include derivatives of galantamine, wherein galantamine is modified by making non-toxic acid addition salts thereof. Examples of pharmaceutically acceptable salts include, but are not limited to, mineral or organic acid addition salts of basic residues such as amines; alkali or organic addition salts of acidic residues such as carboxylic acids; and the like, or a combination comprising at least one of the foregoing salts.

The pharmaceutically acceptable salts include salts of the parent compound formed, for example, from non-toxic inorganic or organic acids. For example, non-toxic acid salts include those derived from inorganic acids such as hydrochloric, hydrobromic, sulfuric, sulfamic, phosphoric, nitric and the like. Pharmaceutically acceptable organic salts include salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like. Combinations comprising at least one of the foregoing salts may also be used.

A particularly useful salt of galantamine is galantamine hydrobromide (1:1).

The controlled-release formulations described herein provide desirable properties and advantages. The formulations can be administered once daily or even less frequently, which is particularly desirable for this active ingredient. The formulation can provide many inherent therapeutic benefits that are not achieved with corresponding short acting, immediate-release preparations. For example, the formulation can provide optimal effective plasma levels of galantamine over an extended period of time. In addition, the formulation can maintain low, steady plasma peak values, for example, $C_{max}$, so as to reduce the incidence and severity of possible side effects.

Furthermore, the controlled-release formulations are desirable as they may reduce cholinergic side affects associated with the use of galantamine, such as gastric irritation. Thus, the controlled-release formulation can provide initial low levels of galantamine into the plasma, avoiding an initial burst of this active ingredient which helps to reduce acute cholinergic effects of galantamine.

The core of the controlled-release formulation comprises a water insoluble polymer and galantamine as the active ingredient, wherein the core is free of a water soluble excipient. The core can further comprise a core substrate where the insoluble polymer, galantamine, and optional excipients are provided as a core coating layer surrounding the core substrate.

The core coating layer may comprise galantamine as the active ingredient, a water insoluble polymer, optionally a plasticizer, and optionally other suitable pharmaceutical excipients, for example, those which may be useful in improving stability and mechanical properties of the core coating layer and/or the formulation.

The water insoluble polymer in the core coating layer may serve as a binder. It is worth noting that a person skilled in the art would readily appreciate that some excipients may serve more than one function. For example, ethyl cellulose may serve as a binder and/or a release rate controlling excipient.

Materials suitable for use as the water insoluble polymer in the core include, but are not limited to, water insoluble cellulosic polymers such as ethyl cellulose, microcrystalline cellulose, cellulose acetate, cellulose diacetate, and cellulose triacetate; water insoluble polymers such as polyvinyl acetate, and polymethacrylates including amino methacrylate copolymers such as EUDRAGIT RS, EUDRAGIT RL, and EUDRAGIT NE30D; and a combination comprising at least one of the foregoing water insoluble polymers. EUDRAGIT RS and EUDRAGIT RL are copolymers of poly(methacrylic acid, methylmethacrylate). The molar ratio of ammonium groups to the remaining neutral (meth)acrylic esters is 1:20 in EUDRAGIT RL 30 D and 1:40 in EUDRAGIT RS 30 D. The mean molecular weight is about 150,000. The code designations RL (high permeability) and RS (low permeability) refer to the permeability properties of these agents). EUDRAGIT polymers are commercially available from Rohm Pharma GmbH, Germany.

The water insoluble polymer may be present in the core coating layer from about 5 weight percent (wt %) to about 50 wt %, specifically about 10 wt % to about 40 wt %, or more specifically about 15 wt % to about 30 wt %, based on the total weight of the core coating layer.

Suitable optional plasticizers for use in the core coating layer include, but are not limited to, dibutyl sebacate, diethyl phthalate, and triethyl citrate. When present, the plasticizer may be present in the core coating layer in an amount of about 0.1 wt % to about 25 wt %, specifically about 0.5 wt % to about 15 wt %, or more specifically about 1.0 wt % to about 10 wt %, based on the total weight of the core coating layer.

Materials suitable for use as the core substrate include, but are not limited to, pharmaceutically acceptable excipients provided that they have appropriate dimensions and firmness. Examples of suitable core substrate excipients include, for example, water insoluble cellulosic polymers such as microcrystalline cellulose, ethyl cellulose, cellulose acylate, cellulose diacylate, cellulose triacylate, cellulose monoacetate, cellulose diacetate, cellulose triacetate, sodium carboxymethyl cellulose, monocellulose alkanylate, dicellulose alkanylate, tricellulose alkanylate, monocellulose alkenylates, dicellulose alkenylates, tricellulose alkenylates, monocellulose aroylates, dicellulose aroylates, tricellulose aroylates, or a combination comprising at least one of the foregoing polymers; plastic resins; inorganic substances, for example, silica, glass, hydroxyapatite, and the like; and certain water insoluble organic substances, for example, activated carbon. Water insoluble cellulosic polymers described above are particularly useful as the core substrate.

The core substrate materials may be present in the core in an amount of about 10 wt % to about 99 wt %, or, more specifically, about 40 wt % to about 95 wt %, or, even more specifically, about 60 wt % to about 90 wt %, based on the total weight of the core.

The core may have a mean diameter of about 100 to about 2,500 micrometers, specifically about 150 to about 2,000 micrometers, or more specifically about 250 to about 1,500 micrometers. The particle sizes mentioned herein can be obtained, for example, by sieving the core substrate material through nominal standard test sieves as described in the CRC Handbook, 64th ed., page F-114. Nominal standard sieves are characterized by the mesh/hole width (μm), DIN 4188 (mm), ASTM E 11-70 (No.), Tyler® (mesh) or BS 410 (mesh) standard values.

In one embodiment, the core comprises a core substrate of microcrystalline cellulose and a core coating layer comprising galantamine hydrobromide (1:1) as the active ingredient, ethyl cellulose as binder, and dibutyl sebacate as plasticizer. The core is free of a water soluble excipient such as hydroxypropyl methylcellulose.

The weight-by-weight ratio of galantamine in the core coating layer to the core substrate material can be in the range of about 1:50 to about 10:1, specifically about 1:20 to about 5:1, or more specifically about 1:10 to about 1:1. The exact weight ratios may be determined by a person of ordinary skill in the art without undue experimentation and may be affected by practical considerations such as desired capsule fill weight.

The weight-by-weight ratio of galantamine to the water insoluble polymer in the core coating layer is in the range of about 20:1 to about 1:10, or specifically about 10:1 to about 1:3, or more specifically about 5:1 to about 1:1. The exact weight ratios may be determined by a person of ordinary skill in the art without undue experimentation and may be affected by practical considerations such as efficiency of drug binding with minimal drug loss.

In one embodiment, the microcrystalline cellulose core substrate, the active ingredient galantamine hydrobromide (1:1), the ethyl cellulose binder, and the plasticizer dibutyl sebacate are present in the core in an amount of about 50 wt %-90 wt %, about 5 wt %-20 wt %, about 1 wt %-10 wt %, and about 0.01 wt %-about 5 wt %, respectively, based on the total weight of the core.

A release rate controlling coating substantially surrounds the core. As used herein, "substantially surround" means the release rate controlling coating covers about 80% or more of the total surface area of the core (bead, pellet, particle, sphere, etc.), specifically about 90% or more, more specifically about 95% or more, or even more specifically about 99% or more, of the total surface area of the core.

The release rate controlling coating comprises a release retarding excipient, optionally a pore forming excipient, optionally a plasticizer, and optionally other suitable pharmaceutical excipients that may improve stability, compatibility, mechanical, or flow properties of the coating and/or the formulation. The release retarding excipient may be a water soluble or water insoluble polymer. The polymer in the release rate controlling coating layer may be the same or different as the polymer in the core coating layer. For example, the core coating layer may include a water insoluble polymer while the release rate controlling coating may include a water soluble filler.

Suitable water insoluble release retarding excipients include, but are not limited to, water insoluble cellulosic polymers such as ethyl cellulose, cellulose acetate, cellulose diacetate, and cellulose triacetate; water insoluble polymers such as polyvinyl acetate; and polymethacrylates including amino methacrylate copolymers. Exemplary polymethacrylates include EUDRAGIT RS (poly[ethyl acrylate, methyl methacrylate, trimethylammonioethyl methacrylate chloride] 1:2:0.1, CAS No. 33434-24-1), EUDRAGIT RL (poly[ethyl acrylate, methyl methacrylate, trimethylammonioethyl methacrylate chloride] 1:2:0.2,CAS No. 33434-24-1); Eudragit NE30D (poly[ethylacrylate, methyl methacrylate] 2:1, CAS No. 9010-88-2); and the like. Suitable water soluble release retarding excipients include, but are not limited to, water soluble polymers such as povidone, hydroxylpropyl methylcellulose (HPMC), hydroxypropyl cellulose (Klucel), and polyethylene glycols (PEG) such as PEG 1000, PEG 1450, PEG 1500, and PEG 6000.

The release retarding excipient may be present in the release rate controlling coating in an amount of about 30 wt % to about 90 wt %, specifically about 50 wt % to about 80 wt %, or more specifically about 60 wt % to about 70 wt %, based on the total weight of the release rate controlling coating.

The optional pore forming excipients in the release rate controlling coating include, but are not limited to, water soluble cellulosic polymers such as hydroxypropyl methylcellulose (HPMC) and hydroxypropyl cellulose; water soluble polyethylene glycol (PEG) polymers such as PEG 1000, PEG 1450, PEG 1500, and PEG 6000; and water soluble substances such as sucrose and polyvinyl pyrrolidone (povidone), for example, povidone K30. The povidone polymer can be characterized by its viscosity in an aqueous solution, relative to that of water, expressed as a K-value, ranging from 10 to 120. The approximate weight average molecular weight for povidone K30 is 50,000.

Certain combinations of release retarding excipients and pore forming excipients provide desirable controlled-release properties. Particularly useful combinations include, but are not limited to, ethyl cellulose:povidone, ethyl cellulose:HPMC, ethyl cellulose:hydroxypropyl cellulose, ethyl cellulose:polyethylene glycol, cellulose acetate:povidone, cellulose acetate:HPMC, cellulose acetate:hydroxypropyl cellulose, cellulose acetate:polyethylene glycol, polyvinyl acetate:povidone, polyvinyl acetate:HPMC, polyvinyl acetate:hydroxypropyl cellulose, and polyvinyl acetate:polyethylene glycol. Additional useful combination of polymers as release retarding coating includes EUDRAGIT RS:EUDRAGIT RL.

When pore forming excipients are present, the weight ratios of release retarding excipient: pore forming excipient in the release rate controlling coating can vary from about 20:1 to about 1:10, specifically from about 10:1 to about 1:5; or more specifically about 5:1 to about 1:1.

Suitable optional plasticizers in the release rate controlling coating include, but are not limited to, dibutyl sebacate, diethyl phthalate, polyethylene glycols, triacetin, acetylated monoglycerides, and triethyl citrate. When present, the plasticizer can be present in an amount of about 0.1 wt % to about 30 wt %, specifically about 1 wt % to about 20 wt %, or more specifically about 2 wt % to about 15 wt %, based on the total weight of the release rate controlling coating.

The rate of release of the active ingredient galantamine from the controlled-release formulation is approximately inversely proportional to the weight or thickness of the release rate controlling coating. In addition, the release profile of galantamine (either in vivo or in vitro) can be altered, for example, by using more than one release retarding excipient, varying the thickness of the release retarding excipient, changing the particular release retarding excipient used, altering the relative amounts of release retarding excipient, altering the manner in which the plasticizer is added, varying the amount of plasticizer relative to release retarding excipient, by the inclusion of additional ingredients or excipients, or by altering the method of manufacture, etc.

In one embodiment, the release rate controlling coating comprises ethyl cellulose, povidone K30, and dibutyl sebacate. In another embodiment, the ethyl cellulose, povidone K30, and dibutyl sebacate are present in the coating in an amount of about 40 wt % to about 80 wt %, about 10 wt % to about 30 wt %, and about 5 wt % to about 20 wt %, respectively, based on the total weight of the release rate controlling coating.

Both the core coating layer and the release rate controlling coating may further optionally comprise other pharmaceutical excipients that may improve stability, compatibility, mechanical, or flow properties of the formulation, for example, thickening agents; surfactants; preservatives; complexing and chelating agents; lubricants such as talc or magnesium stearate; glidants such as fumed or colloidal silica; pH modifiers such as acids, bases, or buffer systems; pharmaceutically useful processing aids; or a combination comprising at least one of the foregoing excipients. The formulation may also contain other active ingredients.

The core may be prepared, for example, by dissolving (solution) or dispersing (suspension) the active agent and water insoluble polymer in a suitable solvent and then spraying the solution or suspension onto a core substrate, for example, microcrystalline cellulose particles having suitable particle sizes. Optionally, additional excipients such as binders and/or pore formers can also be added to the galantamine solution or suspension prior to coating the substrates in order to assist the galantamine binding to the substrates.

Suitable solvents used for application of the core coating layer include pharmaceutically acceptable solvents, such as water, methanol, ethanol, methylene chloride, or a combination comprising at least one of the foregoing solvents.

The release rate controlling coating may be applied to the galantamine coated cores in an aqueous dispersion (Aquacoat®, Surelease®), or as a solution in an organic solvent system. Specifically, the release rate controlling coating may be prepared, for example, by dissolving (solution) or dispersing (suspension) the release retarding excipient such as a water insoluble polymer, optionally a pore former such as a water soluble polymer, optionally a plasticizer, and optionally other suitable excipients, in a suitable solvent and then spraying the solution or suspension onto the core.

A useful organic system comprises an alcohol, for example, methanol or ethanol, and optionally a chlorinated hydrocarbon such as for example dichloromethane.

The controlled-release formulation may be in any suitable physical form, and especially in the form of particles, pellets, granules, or spheres. The particles, pellets, granules, or spheres may have a particle size of about 100 to about 3,500 micrometers, specifically about 150 to about 3,000 micrometers, or more specifically about 250 to about 1,500 micrometers.

The controlled-release particles, pellets, granules, or spheres may be filled in hard-gelatin or soft-gelatin capsules such that a therapeutically effective amount of, for example, about 8 to about 24 mg base equivalent of the active ingredient galantamine is available per capsule.

In one embodiment, a controlled-release formulation comprises a core comprising a water insoluble polymer and galantamine as the active ingredient, wherein the core is free of a water soluble excipient; and a release rate controlling coating substantially surrounding the core, wherein the release rate controlling coating comprises a release retarding excipient; wherein the formulation exhibits a dissolution profile such that at 1 hour about 4 to about 9% of the galantamine is released, at 2 hours about 15 to about 25% of the galantamine is released, at 4 hours about 40 to about 55% of the galantamine is released, and at 8 hours about 80 to about 100% of the galantamine is released after combining the dosage formulation with 900 ml of pH 6.5 phosphate buffer at 37° C. in USP Type 1 Apparatus (USP, <711> Dissolution), at a paddle speed of 100 rpm.

The controlled-release formulation may further comprise an immediate release top-coat substantially surrounding the controlled-release particles, pellets, granules, or spheres, wherein the top-coat comprises galantamine, a polymer, optionally a plasticizer, and optionally other suitable pharmaceutical excipients. The galantamine in the top-coat is released practically immediately upon ingestion and produces a rapid onset of action. Through careful control of the amount of the active ingredient in the top-coat and the composition of the top-coat and the overall formulation, the formulation may provide an advantageous pharmacokinetic profile (fast onset, level peak and trough values). For example, advantageous pharmacokinetic profile may be obtained when from about 70 to about 80 wt % of the overall galantamine is comprised within the controlled-release cores and the remaining about 20 to about 30 wt % of the galantamine is comprised in the immediate release top-coat.

In some embodiments, the core comprising the release rate controlling coating may also comprises the immediate release top-coat in the form of a coating partially or even substantially surrounding the core. The immediate release top-coat may be directly in contact with the release rate controlling coating surface or, optionally an intermediate layer of material may be between the immediate release coating and the release rate controlling coating.

Materials suitable for use as the polymer in the top-coat include, but are not limited to, both water soluble and water insoluble polymers. Examples of water insoluble polymers include ethyl cellulose, cellulose acetate, polyvinyl acetate, polymethacrylates including amino methacrylate copolymers such as EUDRAGIT RS, EUDRAGIT RL, and EUDRAGIT NE30D. Examples of water soluble polymers include alkyl celluloses such as methyl celluloses; hydroxyalkyl celluloses such as HPMC, hydroxyethyl cellulose, hydroxypropyl cellulose and hydroxybutyl cellulose; hydroxyalkyl alkyl celluloses such as hydroxyethyl methyl cellulose and hydroxypropyl methyl cellulose; carboxyalkyl celluloses such as carboxymethyl cellulose; alkali metal salts of carboxyalkylcelluloses such as sodium carboxymethylcellulose; carboxyalkyl allyl celluloses such as carboxymethyl ethyl cellulose; carboxyalkyl cellulose esters; starches; pectines such as sodium carboxymethylamylopectine; chitine derivates such as chitosan; polysaccharides such as alginic acid; alkali metal and ammonium salts thereof, carrageenans, galactomannans, traganth, agar-agar, gummi arabicum, guar gummi and xanthan gummi; polyacrylic acids and the salts thereof; polymethacrylic acids and the salts thereof, methacrylate copolymers; polyvinyl alcohol; polyvinyl pyrrolidone, copolymers of polyvinylpyrrolidone with vinyl acetate; polyalkylene oxides such as polyethylene oxide and polypropylene oxide and copolymers of ethylene oxide and propylene oxide.

The polymer in the immediate release top-coat may function as a binder to improve the binding of galantamine to the cores. The polymer may be present in the immediate release top-coat from about 5 wt % to about 50 wt %, specifically about 10 wt % to about 40 wt %, or more specifically about 15 wt % to about 30 wt %, based on the total weight of the top-coat.

Suitable optional plasticizers for top-coat include, but are not limited to, dibutyl sebacate, diethyl phthalate, and triethyl citrate. When present, the plasticizer can be present in an amount of about 0.1 wt % to about 15 wt %, specifically about 0.2 wt % to about 10 wt %, or more specifically about 0.5 wt % to about 5 wt %, based on the total weight of the top-coat.

In one embodiment, the top-coat comprises an ethyl cellulose as binder, galantamine hydrobromide (1:1), and dibutyl sebacate as plasticizer. In another embodiment, the ethyl cellulose binder, galantamine hydrobromide, and the dibutyl sebacate are present in the amount of about 5 wt % to about 30 wt %, about 40 wt % to about 95 wt %, and about 0.1 wt % to about 10 wt %, respectively, based on the total weight of the top-coat.

The controlled-release particles, pellets, granules, or spheres with immediate release top-coat may be in any suitable physical form, and especially in the form of particles, pellets, granules, or spheres.

The controlled-release particles, pellets, granules, or spheres with immediate release top-coat may have a particle size of about 100 to about 3,500 micrometers, specifically about 150 to about 2,500 micrometers, or more specifically about 250 micrometers to about 1,500 micrometers. These particles, pellets, granules, or spheres may be filled in hard-gelatin or soft-gelatin capsules, optionally in combination with cores.

The controlled-release particles, pellets, granules, or spheres (with or without top-coat), optionally with immediate release top-coat, may also be compressed into tablets using excipients suitable for direct compression such as saccharides, cellulosic excipients, starches, and the like. Care should be taken in the tableting process to ensure content uniformity and coating integrity, especially in direct compression tableting processes. Suitable direct compression excipients can be found in copending application Ser. No. 11/133,864 filed May 20, 2005 which is incorporated herein in its entirety.

A compressible mixture comprising the controlled-release particles, pellets, granules, or spheres (with or without top-coat), a compression filler such as a waxy filler, a cellulose filler, or a mixture thereof and a disintegrant may be used to prepare tablets containing controlled-release galantamine particles. Exemplary waxy fillers include waxes such as carnauba wax (from the palm tree Copernicia Cerifera), vegetable wax, fruit wax, microcrystalline wax ("petroleum wax"), bees wax (white or bleached, and yellow), hydrocarbon wax, paraffin wax, cetyl esters wax, non-ionic emulsifying wax, anionic emulsifying wax, candelilla wax, a combination comprising at least one of the foregoing, and the like. Other suitable waxy fillers include, for example, stearyl alcohol, cetyl alcohol, cetostearyl alcohol, PEG having a molecular weight of greater than about 3000 number average molecular weight, $M_n$ (e.g. PEG 3350, PEG 4000, PEG 4600, PEG 6000, and PEG 8000). Each wax described herein can be in powder or flake form. Exemplary cellulose fillers include powdered cellulose having a "cottony" or "fluffy" characteristic (non-flowing), or microcrystalline cellulose (e.g., Avicel PH101 and Avicel PH102).

As used herein, "disintegrant" means an agent used in a formulation, (e.g. tablet or capsule) to aid in the break down of a compacted mass in the presence of a fluid environment, specifically aqueous environments. The choice and amount of disintegrant can be tailored to ensure the dissolution profile of the tablet is substantially the same as the dissolution profile of the drug particles alone. In an alternative embodiment, the choice and amount of disintegrant is tailored to provide additional release-retarding properties for those formulations where additional controlled-release is desired.

Additional optional excipients for making tablets include, for example, silicified microcrystalline cellulose, powdered cellulose, polyvinyl pyrrolidone, hydroxypropyl cellulose, hydroxypropyl methylcellulose, methylcellulose hydroxyethyl cellulose, mannitol, sorbitol, lactose, digestible sugars, sucrose, liquid glucose, sorbitol, dextrose, isomalt, liquid maltitol, aspartame, lactose, talc, and the like, or a combination comprising at least one of the foregoing.

The compressible mixture can further comprise a lubricant and/or glidant to aid in the tableting process. Exemplary lubricants include stearic acid, stearates (e.g., calcium stearate, magnesium stearate, and zinc stearate), sodium stearyl fumarate, glycerol behenate, mineral oil, polyethylene glycol, talc, vegetable oil, or a combination comprising at least one of the foregoing. Glidants include, for example, silicon dioxide (e.g. fumed or colloidal). Certain materials can function both as a glidant and a lubricant.

Certain formulations described herein may be coated with a coating layer. The coating can be, for example, a functional or a non-functional coating, or multiple functional and/or non-functional coatings. By "functional coating" is meant to include a coating that modifies the release properties of the formulation, for example, a release rate controlling coating. By "non-functional coating" is meant to include a coating that is not a functional coating, for example, a cosmetic coating. A non-functional coating can have some impact on the release of the active ingredient due to the initial dissolution, hydration, perforation of the coating, etc., but would not be considered to be a significant deviation from the non-coated composition.

Disclosed herein also include processes of preparing controlled-release formulations as described hereinbefore comprising admixing galantamine with a water insoluble polymer to form a core, and applying the release rate controlling coating to the core.

In one embodiment, the core disclosed herein may be conveniently prepared in the following manner. A core coating solution or suspension is prepared by dissolving into a suitable solvent system appropriate amounts of a water insoluble polymer, optionally a suitable plasticizer, and galantamine, for example galantamine HBr (1:1). A suitable solvent system comprises purified water or an alcohol, preferably ethanol.

The core coating process (e.g., core coating, release rate controlling coating, and top-coating) may be conveniently conducted in a fluidized bed granulator equipped with a bottom spray insert. The process parameters depend on the equipment used and materials processed. In one embodiment, water insoluble polymers such as microcrystalline cellulose particles are loaded into the product container of the granulator. Then, the drug solution or suspension is sprayed onto the water insoluble polymer particles. The spray rate, air volume, and inlet air temperature can be adjusted to get optimum coating. After the completion of coating, the resulting drug loaded cores can be dried, for example at about 15 to about 60° C.

The spraying rate can be regulated to prevent loss of drug product by too low a spraying rate or agglomeration by too high a spraying rate.

The release rate controlling coating may be conveniently prepared in the following manner. A release rate controlling coating solution or suspension is prepared by dissolving into a suitable solvent system appropriate amounts of a water soluble or water insoluble polymer, optionally a suitable plasticizer, optionally a pore former, and optionally other suitable additives. A suitable solvent system comprises purified water or an alcohol, preferably ethanol. The solution can be stirred during the coating process. The controlled-release coating solution or suspension may be conveniently sprayed onto the cores in a fluidized bed granulator in a similar manner as described above under the core coating process.

The controlled-release formulations with immediate release top-coat may be conveniently prepared in the following manner. First, a top-coat solution or suspension is prepared by dissolving into a suitable solvent system appropriate amounts of a polymer (e.g., water soluble or water insoluble polymer), optionally a suitable plasticizer, and galantamine, for example galantamine HBr (1:1). A suitable solvent system comprises purified water or an alcohol, preferably ethanol. The solution may be stirred during the coating process. Then, the immediate release top-coat solution or suspension is sprayed onto controlled-release particles or pellets described above in a fluidized bed granulator in a similar manner as described above under the core coating process.

By "RAZADYNE ER" is meant galantamine hydrobromide formulations manufactured by Ortho-McNeil Neurologics, Inc., a drug product associated with New Drug Application Number 021615. Specifically, by RAZADYNE ER is meant opaque hard gelatin extended release capsules of galantamine hydrobromide, base equivalent of 8, 16, and 24 mg, in the presence of inactive ingredients of gelatin, diethyl phthalate, ethyl cellulose, hypromellose, propylene glycol, titanium dioxide, and sugar spheres (sucrose and starch), optionally yellow ferric oxide (24 mg capsule), red ferric oxide (16 mg capsule).

In one embodiment, the controlled-release formulations described herein preferably exhibit bioequivalence to the marketed drug product, for example RAZADYNE ER (New Drug Application number 021615). Bioequivalence is defined as "the absence of a significant difference in the rate and extent to which the active ingredient or active moiety in pharmaceutical equivalents or pharmaceutical alternatives becomes available at the site of drug action when administered at the same molar dose under similar conditions in an appropriately designed study" (21 CFR 320.1). The determination of bioequivalence can be made, for example, according to the Federal Drug Administration's (FDA) guidelines and criteria, including "GUIDANCE FOR INDUSTRY BIOAVAILABILITY AND BIOEQUVALENCE STUDIES FOR ORALLY ADMINISTERED DRUG PRODUCTS—GENERAL CONSIDERATIONS" available from the U.S. Department of Health and Human Services (DHHS), Food and Drug Administration (FDA), Center for Drug Evaluation and Research (CDER) March 2003 Revision 1; and "GUIDANCE FOR INDUSTRY STATISTICAL APPROACHES TO ESTABLISHING BIOEQUIVALENCE" DHHS, FDA, CDER, January 2001.

EXAMPLES

The following examples further illustrate the invention but, of course, should not be construed as in any way limiting its scope.

Example 1

Galantamine Hydrobromide (1:1) Cores

The composition of the galantamine hydrobromide (1:1) cores is shown in Table 1.

TABLE 1

| Core composition | | |
|---|---|---|
| Ingredient | Amount/Batch, kg | Weight % of core |
| Galantamine hydrobromide (1:1) | 1.230 | 12.3 |
| Microcrystalline cellulose spheres | 8.364 | 8.36 |
| Ethyl cellulose, 45 cps | 0.369 | 3.69 |
| Dibytul sebacate | 0.037 | 0.37 |
| Ethanol[1] | 9.300 | |

[1]This ingredient is not present in the end product.

The cores are prepared in the following manner. First, a core coating solution is prepared by dissolving ethyl cellulose (0.369 kg) and dibutyl sebacate (0.037 kg) in ethanol (9.3 kg) followed by dispersing galantamine HBr (1.23 kg) in the resulting solution. Then, the microcrystalline cellulose particles (8.364 kg) are loaded in the product container of GPCG-15 granulator fitted with 9" Wurster. The core coating solution is sprayed onto the microcrystalline cellulose particles. After the completion of coating, the resulting cores are dried at 40° C. in the Wurster.

Example 2

Controlled-release Galantamine Hydrobromide Particles

Controlled-release galantamine hydrobromide (1:1) particles are obtained by coating the galantamine hydrobromide cores obtained in Example 1 with a release rate controlling coating. The composition of the release rate controlling coating is shown in Table 2.

TABLE 2

| Release rate controlling coating composition | | |
|---|---|---|
| Ingredient | Amount/Batch, kg | Weight % of controlled-release coating |
| Galantamine cores | 10 | N/A |
| Polyvinyl pyrrolidone (PVP) K30 | 0.534 | 25.5 |
| Ethyl cellulose, 45 cps | 1.372 | 65.5 |
| Dibytul sebacate | 0.190 | 9.1 |
| Ethanol[1] | 18.90 | |

[1]This ingredient is not present in the end product.

Controlled-release galantamine hydrobromide particles are prepared in the following manner. A release rate control coating solution is prepared by dissolving ethyl cellulose (1.372 kg), PVP K30 (0.534 kg), and dibutyl sebacate (0.19 kg) in ethanol (18.9 kg). The galantamine hydrobromide cores obtained in Example 1 (10 kg) are loaded in the product container of GPCG-15 granulator fitted with 9" Wurster. Next, the release rate control coating solution is sprayed onto the galantamine hydrobromide cores. Three groups of coated samples are collected after 11.5 wt. %, 12 wt. %, and 12.5 wt. % of coating polymer is applied, respectively. Finally, all pulled samples are dried at 40° C. in the Wurster.

Dissolution tests are performed on the collected controlled-release particles using USP Type 1 apparatus, phosphate buffer (pH 6.5, 900 mL) is used as the dissolution medium, and the rotation speed is 100 rpm. The wavelength used for quantitation is 230 nm and path length of cuvette is 1 cm. The temperature during the dissolution test is 37±0.5° C. The dissolution results are summarized in Table 3.

TABLE 3

Dissolution data of controlled-release galantamine particles

| | Cumulative release of galantamine % of theoretical amount of galantamine in formulation | | |
|---|---|---|---|
| Time, min | 11.5 wt % coating | 12.0 wt % coating | 12.5 wt % coating |
| 30 | 2 | 2 | 2 |
| 60 | 7 | 7 | 5 |
| 90 | 13 | 12 | 10 |
| 120 | 20 | 19 | 16 |
| 180 | 36 | 33 | 29 |
| 240 | 53 | 49 | 44 |
| 300 | 69 | 64 | 58 |
| 360 | 81 | 76 | 70 |
| 420 | 90 | 86 | 80 |
| 480 | 96 | 93 | 87 |
| 600 | 101 | 100 | 95 |
| 720 | 103 | 103 | 98 |
| 840 | 103 | 104 | 100 |

It can be seen from Table 3 that after the initial period of about 60 minutes, the cumulative release of galantamine generally decreases as the amount of the release rate controlling coating increases from 11.5 wt % to 12.5 wt %.

Example 3

Controlled-release Galantamine Hydrobromide Particles with Immediate Release Top-coat Controlled-release galantamine hydrobromide particles obtained in Example 2 are further coated with an immediate release top-coat to obtain desirable release properties. The composition of the immediate release top-coat is shown in Table 4.

TABLE 4

Immediate release top-coat composition

| Ingredient | Amount/Batch, kg |
|---|---|
| Galantamine hydrobromide controlled-release pellets | 11.764 |
| Galantamine hydrobromide | 0.527 |
| Ethyl cellulose, 45 cps | 0.158 |
| Dibytul sebacate | 0.016 |
| Ethanol[1] | 4.0 |

[1]This ingredient is not present in the end product.

Controlled-release galantamine hydrobromide (1:1) particles with immediate release top-coat are prepared in the following manner. A top-coat solution is made by dissolving ethyl cellulose (0.158 kg) and dibutyl sebacate (0.016 kg) in ethanol (4.0 kg) followed by dispersing galantamine hydrobromide (0.527 kg) in the resulting solution. The galantamine hydrobromide controlled-release particles obtained in Example 2 are loaded in the product container of GPCG-15 granulator fitted with 9" Wurster. The immediate release top-coat solution is sprayed onto the galantamine hydrobromide controlled-release pellets. Finally, all top-coated samples are dried at 40° C. in the Wurster.

Example 4

Hard-gelatin Capsules

The controlled-release galantamine hydrobromide particles obtained in Example 2 and/or the controlled-release galantamine hydrobromide particles with immediate release top-coat obtained in Example 3 are filled into hard-gelatin capsules to give 8, 16, and 24 mg base equivalent doses.

Example 5

Tablets

The controlled-release galantamine hydrobromide particles obtained in Example 2 and/or the controlled-release galantamine hydrobromide particles with immediate release top-coat obtained in Example 3 are mixed with a compressible excipient and the resulting mixture is compressed into tablets to give 8, 16, and 24 mg base equivalent doses.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including", and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A controlled-release dosage formulation, comprising:
a core consisting of a core coating layer of 5 wt % to 50 wt % of a water insoluble polymer and 0.1 wt % to 25 wt % of a plasticizer, based on the weight of the core coating layer, in admixture with galantamine as the active ingredient, wherein the core coating layer is deposited onto a core substrate to form the core, wherein the core is free of a water soluble excipient; and a release rate controlling coating substantially surrounding the core, wherein the release rate controlling coating comprises 30 wt % to 90 wt % of a release retarding polymer; and a pore forming excipient comprising a water soluble polymer in an amount of 20:1 to 1:10 release retarding polymer: pore forming excipient; and 0.1 wt % to 30 wt % of a plasticizer, wherein the formulation exhibits a dissolution profile such that at 1 hour about 4 to about 9% of the galantamine is released, at 2 hours about 15 to about 25% of the galantamine is released, at 4 hours about 40 to about 55% of the galantamine is released, and at 8 hours about 80 to about 100% of the galantamine is released after combining the dosage formulation with 900 ml of pH 6.5 phosphate buffer at 37° C. in USP Type 1 Apparatus (USP, <711> Dissolution), at a paddle speed of 100 rpm.

2. The dosage formulation of claim 1, wherein the core substrate material is a water insoluble cellulosic polymer, a plastic resin, silica, glass, hydroxyapatite, or activated carbon.

3. The dosage formulation of claim 1, wherein the water insoluble polymer is a water insoluble cellulosic polymer, a polyvinyl acetate, or a polymethacrylate.

4. The dosage formulation of claim 3, wherein the water insoluble cellulosic polymer is ethyl cellulose, microcrystalline cellulose, cellulose acetate, cellulose diacetate, cellulose triacetate, or a combination comprising at least one of the foregoing water insoluble celluloses.

5. The dosage formulation of claim 3, wherein the water insoluble cellulosic polymer is ethyl cellulose.

6. The dosage formulation of claim 1, wherein the release retarding polymer is a water insoluble cellulosic polymer, a polyvinyl acetate, a polymethacrylate, or a combination comprising at least one of the foregoing release retarding excipients.

7. The dosage formulation of claim 6, wherein the water insoluble cellulosic polymer is ethyl cellulose, cellulose acetate, cellulose diacetate, cellulose triacetate, or a combination comprising at least one of the foregoing water insoluble cellulosic polymers.

8. The dosage formulation of claim 7, wherein the water insoluble cellulosic polymer is ethyl cellulose.

9. The dosage formulation of claim 1, wherein the water soluble polymer is povidone, hydroxypropyl methylcellulose, hydroxypropyl cellulose, polyethylene glycol, or a combination comprising at least one of the foregoing water soluble polymers.

10. The dosage formulation of claim 1, wherein the release rate controlling coating comprises ethyl cellulose and povidone K30.

11. The dosage formulation of claim 1, further comprising an immediate release top-coat, wherein the immediate release top-coat comprises a polymer and galantamine.

12. The dosage formulation of claim 11, wherein the polymer is a water soluble or a water insoluble polymer.

13. The dosage formulation of claim 12, wherein the water insoluble polymer is ethyl cellulose, cellulose acetate, polyvinyl acetate, a polymethacrylate, or a combination comprising at least one of the foregoing water insoluble polymers.

14. The dosage formulation of claim 12, wherein the water insoluble polymer is ethyl cellulose.

15. The dosage formulation of claim 12, wherein the water soluble polymer is an alkyl cellulose; a hydroxyalkyl cellulose; a hydroxyalkyl alkyl cellulose; a carboxyalkyl cellulose; an alkali metal salts of a carboxyalkylcellulose; a carboxyalkyl alkyl cellulose; a carboxyalkyl cellulose ester; a starches; a pectin; a chitine derivate; a polysaccharide; carrageenan; galactomannan; traganth; agar-agar; gummi arabicum;guar gummi; xanthan gummi; a polyacrylic acid; a polymethacrylic acid; a methacrylate copolymer;

a polyvinyl alcohol; a polyvinyl pyrrolidone; a copolymer of polyvinylpyrrolidone with vinyl acetate; a polyalkylene oxide; a copolymer of ethylene oxide and propylene oxide; or a combination comprising at least one of the foregoing water soluble polymers.

16. The dosage formulation of claim 12, wherein the water soluble polymer is hydroxypropyl methylcellulose.

17. A dosage formulation, comprising:

a core consisting of a core coating layer of 5 wt % to 50 wt % of a water insoluble cellulosic polymer and 0.1 wt % to 25 wt % of a plasticizer, based on the weight of the core coating layer, in admixture with galantamine as the active ingredient, wherein the core coating layer is deposited onto a core substrate to form the core, wherein the core is free of a water soluble excipient; and a release rate controlling coating substantially surrounding the core, wherein the release rate controlling coating comprises 30 wt % to 90 wt % of a water insoluble cellulosic polymer; and a pore forming excipient comprising a water soluble polymer in an amount of 20:1 to 1:10 water insoluble cellulosic polymer: pore forming excipient; and 0.1 wt % to 30 wt % of a plasticizer;

wherein the formulation exhibits a dissolution profile such that at 1 hour about 4 to about 9% of the galantamine is released, at 2 hours about 15 to about 25% of the galantamine is released, at 4 hours about 40 to about 55% of the galantamine is released, and at 8 hours about 80 to about 100% of the galantamine is released after combining the dosage formulation with 900 ml of pH 6.5 phosphate buffer at 37° C. in USP Type 1 Apparatus (USP, <711> Dissolution), at a paddle speed of 100 rpm.

18. The dosage formulation of claim 1 or 11, wherein the formulation is in the form of tablets, particles, pellets, granules, or spheres, wherein the particles, pellets, granules, or spheres have a particle size of about 100 to about 2,500 micrometers.

19. A method of treating a disorder selected from dementia, mania, or nicotine dependence in a patient in need thereof comprising administering to the patient the dosage formulation of claim 1.

* * * * *